(12) United States Patent
Malul

(10) Patent No.: US 9,232,987 B2
(45) Date of Patent: Jan. 12, 2016

(54) TIP EXTENSION FOR DIFFICULT TO CALIBRATE HANDPIECE

(71) Applicant: Image Navigation, Inc., New York, NY (US)

(72) Inventor: Uri Malul, Beachwood, OH (US)

(73) Assignee: IMAGE NAVIGATION, INC., New York, NY (US)

( * ) Notice: Subject to any disclaimer, the term of this patent is extended or adjusted under 35 U.S.C. 154(b) by 135 days.

(21) Appl. No.: 13/905,152

(22) Filed: May 30, 2013

(65) Prior Publication Data

US 2014/0357982 A1     Dec. 4, 2014

(51) Int. Cl.
| | |
|---|---|
| *A61B 5/06* | (2006.01) |
| *A61C 3/025* | (2006.01) |
| *A61C 1/07* | (2006.01) |
| *A61C 3/03* | (2006.01) |
| *A61B 17/3203* | (2006.01) |
| *A61C 1/08* | (2006.01) |
| *A61B 17/00* | (2006.01) |
| *A61B 19/00* | (2006.01) |

(52) U.S. Cl.
CPC .................. *A61C 3/025* (2013.01); *A61B 5/061* (2013.01); *A61B 17/3203* (2013.01); *A61B 19/5244* (2013.01); *A61C 1/07* (2013.01); *A61C 1/08* (2013.01); *A61C 3/03* (2013.01); *A61B 5/064* (2013.01); *A61B 2017/00725* (2013.01); *A61B 2017/32032* (2013.01); *A61B 2017/32035* (2013.01); *A61B 2019/527* (2013.01); *A61B 2019/5255* (2013.01); *Y10T 29/49716* (2015.01)

(58) Field of Classification Search
CPC .................. A61B 17/3203; A61B 2017/32032; A61B 2017/32035; A61B 5/065; A61C 1/07; A61C 3/025; A61C 3/03
USPC .................. 600/424; 606/167, 169; 29/401.1
See application file for complete search history.

(56) References Cited

U.S. PATENT DOCUMENTS

| | | | |
|---|---|---|---|
| 6,216,573 B1 * | 4/2001 | Moutafis et al. | 83/177 |
| 6,434,507 B1 * | 8/2002 | Clayton et al. | 702/152 |
| 7,457,443 B2 | 11/2008 | Persky | |

* cited by examiner

*Primary Examiner* — Michael Rozanski
(74) *Attorney, Agent, or Firm* — Mark M. Friedman

(57) ABSTRACT

An apparatus for use with an image-guided system to calibrate a handpiece having a tip that is difficult to calibrate comprises a tip extension having an attachment end and a round end, the attachment end configured to fixedly attach to the tip of the handpiece. The attachment end may include a female component that mates with a correspondingly shaped male component of the tip of the handpiece. The tip extension may have a neck configured to allow rotation of the round end when the round end is in a round recess. A method of using an image-guided system to calibrate a handpiece having a tip may comprise fixedly attaching to the tip an attachment end of a tip extension, the tip extension also having a round end separate from the attachment end; and calibrating a center of the round end by contacting the round end to a calibration device.

41 Claims, 8 Drawing Sheets

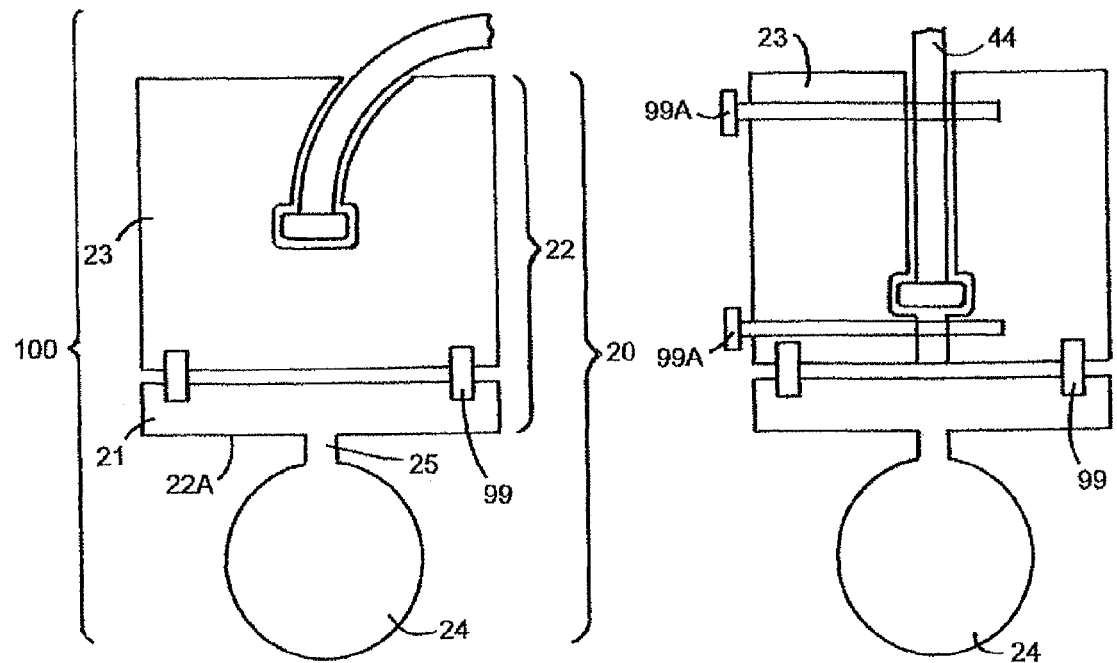
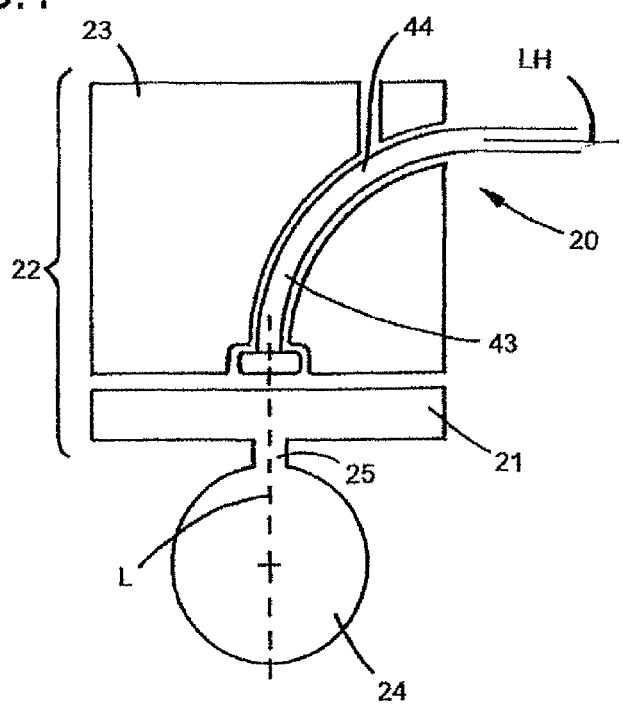

METHOD - 400

PROVIDING A PLURALITY OF TIP EXTENSIONS, EACH TIP EXTENSION OF THE PLURALITY OF TIP EXTENSIONS HAVING AN ATTACHMENT END AND A ROUND END, THE ATTACHMENT END FIXEDLY ATTACHABLE TO THE TIP OF AT LEAST A PLURALITY OF THE HANDPIECES, THE ROUND END CONFIGURED TO BE CALIBRATED FOR THE IMAGE-GUIDED SYSTEM BY INSERTING THE ROUND END IN A CALIBRATION DEVICE HAVING A ROUND RECESS

410

CONFIGURING PARTICULAR TIP EXTENSIONS TO BE USABLE WITH PARTICULAR HANDPIECES OF THE VARIETY OF HANDPIECES BY CONFIGURING A LENGTH OF EACH OF A PLURALITY OF THE PARTICULAR TIP EXTENSIONS SUCH THAT A DISTANCE FROM THE CENTER OF ACTION TO A CENTER OF THE ROUND END REMAINS CONSTANT

TIP EXTENSION FOR DIFFICULT TO CALIBRATE HANDPIECE

FIELD AND BACKGROUND OF THE INVENTION

The present invention relates to calibration of handpieces that make cavities, and, more particularly for calibration of such handpieces that have a tip whose position is difficult to, or cannot be, calibrated by image-guided systems.

Image-guided navigation of surgical handpieces, such as dental handpieces, is well-known. For example, U.S. Pat. No. 7,457,443 to Persky describes a particular method of compensating for distortions generated in an imaging process, and comprises providing a registration device with a plurality of markers disposed in a predetermined three-dimensional pattern, the markers being rendered visible in the imaging process; producing a scanned image of an object of interest in the presence of the registration device; and correcting the data of said scanned image such that the image of the markers accurately reproduces the predetermined three-dimensional pattern. This image-guided navigation is typically used for dental handpieces that are used to drill teeth by means of the rotation of a shaft connected to a symmetrically shaped drill bit that causes cavitation.

The problem is that with the advent of new technologies for drilling bone, certain surgical handpieces, including dental handpieces, may have tips whose position cannot as a practical matter, or without great difficulty or cannot at all, be precisely defined or calibrated using known image-guided systems, for example because the tips of the handpieces have an irregular shape. Such handpieces may make holes, for example in bone, by means of other technologies rather than by ordinary drilling by rotation. For example, some handpieces induce cavitation by shooting high pressure steam through a tiny curved or twisted hose tip. As shown in FIG. 1, a handpiece for steam-based cavitation may shoot steam through a curved or irregularly shaped tip. In other cases, the handpieces cut bone using ultrasonic vibration or energy.

For handpieces using these other non-rotary drilling technologies, in which the tip of the handpiece may be shaped irregularly, or the end of the tip or the line of action of the handpiece is not along the longitudinal axis of the handpiece, calibration of the tip of the handpiece may be too difficult or impractical or even impossible using the known image-guided technologies. The shape of the tip may be too difficult or impossible to be precisely defined by the image-guided system. For the surgery by image-guided system to succeed, however, calibration of the tip of the handpiece is essential. It is well known that in dental and other surgeries, precision is an essential ingredient to a successful operation.

There is a compelling need for an apparatus, system and/or method of calibration for cavitation-inducing handpieces, the position of whose tip is impractical, too difficult or impossible to be defined by known image-guided systems, for example because the tip of the handpiece may have a curved or irregular shape.

SUMMARY OF THE PRESENT INVENTION

One aspect of the present invention is a method of using an image-guided system to calibrate a handpiece having a tip, the method comprising fixedly attaching to the tip an attachment end of a tip extension, the tip extension also having a round end separate from the attachment end; and calibrating a center of the round end by contacting the round end to a calibration device.

A further aspect of the present invention is a method of cavitation of a bone of a human or animal using an image-guided system to calibrate a handpiece having a tip, the method comprising fixedly attaching to the tip an attachment end of a tip extension, the tip extension also having a round end separate from the attachment end; calibrating a center of the round end by contacting the round end to a calibration device; removing the tip extension from the handpiece; and using the handpiece to make a cavity in the bone using the image-guided system.

A still further aspect of the present invention is a method of making tip extensions suitable for a variety of handpieces made by a plurality of different manufacturers and that have a defined center of action that may vary from one manufacturer to another, each of the handpieces having a tip such that the tip is not aligned with the line of action of the handpiece, the method comprising providing a plurality of tip extensions, each tip extension of the plurality of tip extensions having an attachment end and a round end, the attachment end fixedly attachable to the tip of at least a plurality of the handpieces, the round end configured to be calibrated for the image-guided system by inserting the round end in a calibration device having a round recess; and configuring particular tip extensions to be usable with particular handpieces of the variety of handpieces by configuring a length of each of a plurality of the particular tip extensions such that a distance from the center of action to a center of the round end remains constant.

A yet still further aspect of the present invention is an apparatus for use with an image-guided system to calibrate a handpiece having a tip, the apparatus comprising a tip extension having an attachment end and a round end, the attachment end configured to fixedly attach to the tip of the handpiece.

A further aspect of the present invention is a tool for cavitation, comprising a handpiece having a tip configured to emit one of pressurized steam and ultrasonic energy waves out of the handpiece, the tip not lying on a line of action of the handpiece; and a tip extension having an attachment end and a round end, the attachment end configured to fixedly attach to the tip of the handpiece.

A still further aspect of the present invention is a tool for cavitation, comprising a handpiece having a tip, the tip not lying on a line of action of the handpiece; and a tip extension having an attachment end and a round end, the attachment end fixedly attached to the tip.

A yet still further aspect of the present invention is a tool for cavitation, comprising a tip of a handpiece, the tip not lying on a line of action of the handpiece and configured to emit one of pressurized steam and ultrasonic energy out of the handpiece; and a tip extension having an attachment end and a round end, the attachment end fixedly attached to the tip.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 4 is a schematic illustration of an apparatus of the present invention, comprising a tip extension fitted on a tip of a handpiece, in accordance with one embodiment of the present invention;

FIG. 4A is a schematic illustration of an apparatus of the present invention, showing a side view of the tip extension of FIG. 4 fitted on a tip of a handpiece, in accordance with one embodiment of the present invention;

FIG. 5 is a schematic illustration of an apparatus of the present invention as in FIG. 4, except also depicting the line of action and center of the round end of the tip extension, in accordance with one embodiment of the present invention;

FIG. 9 is a flow chart showing a still further method in accordance with a further embodiment of the present invention.

DETAILED DESCRIPTION OF THE INVENTION

Figure 1:
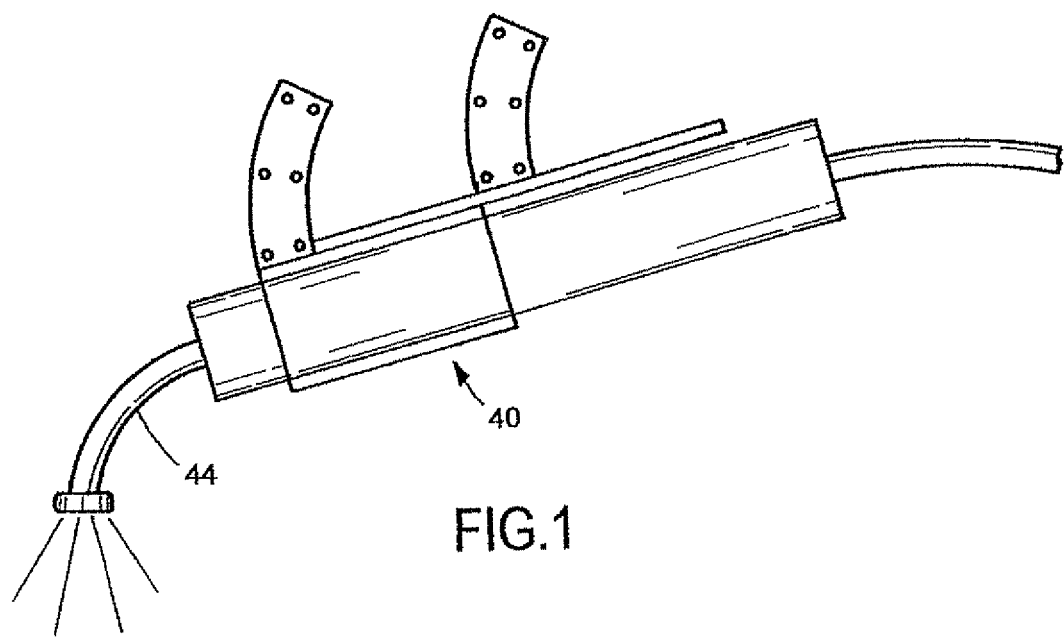
FIG. 1 is a schematic illustration of a prior art handpiece having a tip that emits high pressure steam and having markers to allow tracking by an image-guided system.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides an apparatus and method for calibration of a tip of a handpiece, for example for dental surgery or other bone cutting surgery, where the tip would otherwise be difficult to calibrate by an image-guided system due to the curved or irregular shape of the tip of the handpiece. The surgery may require calibrating the handpiece for the image-guided system prior to a surgery in which the handpiece is used aided by the image-guided navigation system operatively connected to the handpiece. An apparatus of the present invention may comprise a tip extension having an attachment end and a round end, the attachment end configured to fixedly attach to the tip of a handpiece. The attachment end may include a female component that may mate with a correspondingly shaped male component of the tip of the handpiece. The round end may be at least hemispherical and preferably spherical. The tip extension may have a neck that may have a diameter smaller than a diameter of the round end. The neck may be configured to allow the rotation of the round end when the round end is in a round recess of the calibration device such that a center of the round end remains stationary as the round end rotates. The present invention may also comprise the handpiece having a tip, the tip not lying on a longitudinal axis of the handpiece, and the tip extension described above. The present invention may also comprise the tip extension plus just the tip of the handpiece, the tip configured to emit one of pressurized steam and ultrasonic energy out of the handpiece. A method of the present invention may comprise fixedly attaching to the tip an attachment end of a tip extension, the tip extension also having a round end separate from the attachment end; and calibrating a center of the round end by contacting the round end to a calibration device. The method may also include removing the tip extension from the handpiece and using the handpiece to make a cavity in the bone. A method of the present invention may also comprise making or providing tip extensions for a variety of handpieces of different manufacturers whose center of action varies from one manufacturer to the another, the method comprising configuring particular tip extensions to be usable with particular handpieces of the variety of handpieces by configuring the length of each tip extension such that a distance from the center of action to the center of the round end remains constant.

In contrast to prior art handpieces that have tips that are curved or irregular such that they cannot be, or it would be difficult for them to be, calibrated by an image-guided system for surgical cutting, a tool in accordance with one embodiment of the present invention may include a handpiece combined with a tip extension such that when the tip extension is fitted on to the impossible or difficult-to-calibrate tip, the tool may be easily calibrated by a calibration device of an image-guided device. For example, the tip extension may have a female component that may match the corresponding shape of the male component of the tip (or the entire tip) to create an overall shape that may have a defined end that may be along the longitudinal axis of action. In contrast to prior art tips of surgical handpieces, whose end is not on a longitudinal axis of action (line of action) or on a longitudinal axis of the handpiece, in another embodiment, the tip extension itself may lie on the longitudinal axis or line of action of the handpiece and may be relatively easy to calibrate by the image-guided system. In contrast to prior art tips of handpieces that are curved or irregular, the tip plus tip extension of the present invention may be regular and may lie along a longitudinal axis of the handpiece or along the line of action (axis of action) of the handpiece. In contrast to prior art devices that may be compatible with handpieces using one particular drilling technology, the method, apparatus of the present invention may be useful for handpieces that utilize steam cavitation as well as for handpieces that utilize ultrasonic-induced cavitation. In contrast to prior art devices that may be compatible with handpieces or tips of handpieces made by only one particular manufacturer, the method and apparatus of the present invention may be compatible with handpieces or their tips made by a variety of manufacturers. For example, by varying the neck of the apparatus, the distance between the center of action and the center of the round end may be held constant for drill tips of different manufacturers even though the center of action of the handpieces made by the different manufacturers may differ.

The principles and operation of a system for a Tip Extension for Difficult to Calibrate Handpiece may be better understood with reference to the drawings and the accompanying description.

Figure 2:
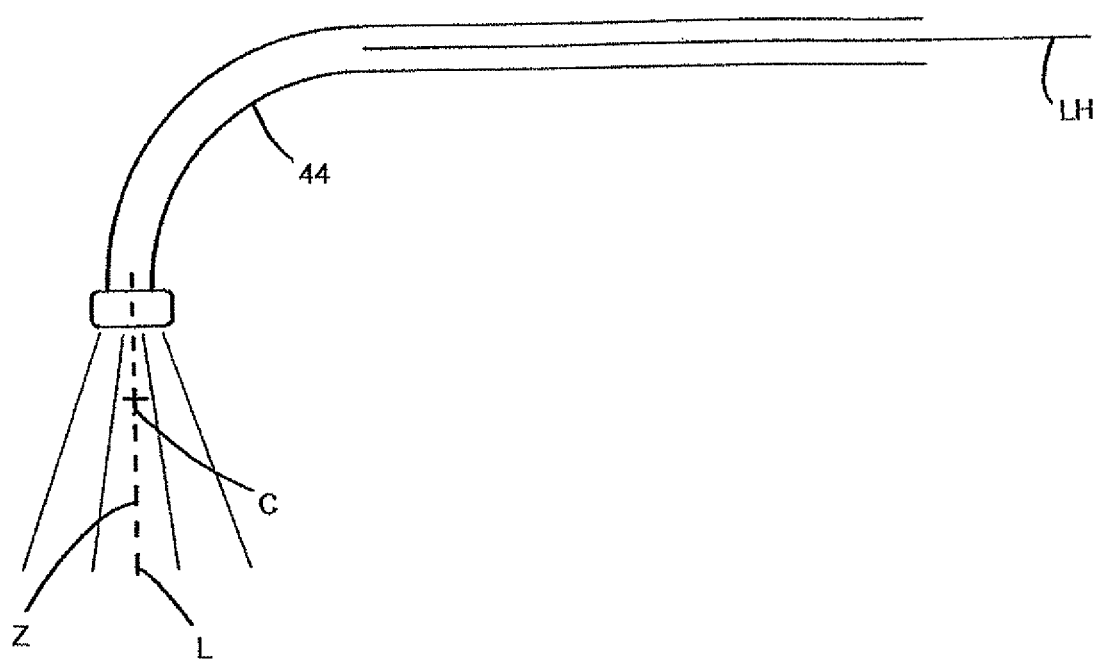
FIG. 2 is a schematic illustration of a prior art tip of a handpiece similar to FIG. 1 showing a center of action and an axis of action.

FIG. 1 depicts a handpiece 40 that may be used for drilling using steam-based cavitation, for example by emitting or shooting steam through a tip 44 under high pressure. Tip 44 is typically curved and/or irregularly shaped. FIG. 2 shows the tip 44 close-up for the purpose of defining concepts such as "line of action" and "center of action". As shown in FIG. 2, the line of action L (sometimes referred to herein as the "axis of action" or the "longitudinal axis of action") represents the direction of the resultant force from what is emitted through the tip, in this case steam. A point "C" along the line of action L is called the "center of action". Point C represents the point along L that is located at the optimum distance from the tip to the surface being drilled, that the user of the handpiece has to maintain. In the case of a typical steam-based drill comprising a dental handpiece, the center of action may be about 0.5 millimeters or typically from about half a millimeter to one millimeter, along the line of action of the shooting steam. The example of the tip shown in FIG. 2 would typically not be calibratable by the image-guided system since its far end, where the steam is emitted, does not lie along the longitudinal axis of the handpiece 40, for example because the far end is curved.

Figure 3:
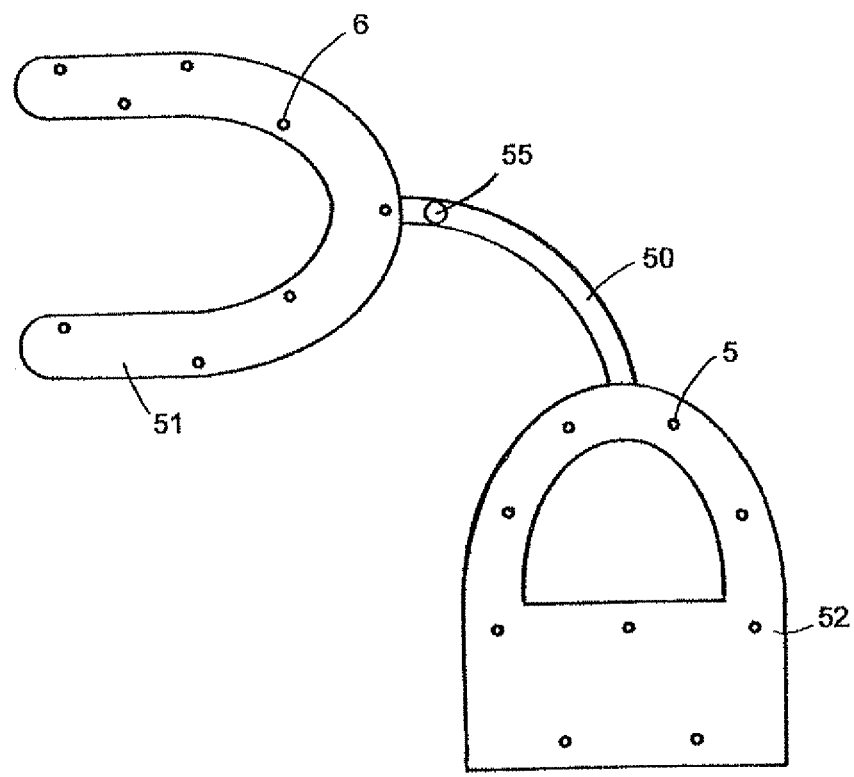
FIG. 3 is a schematic illustration of a calibration, embedded in a registration device, in accordance with one embodiment of the present invention.

FIG. 3 shows a calibration device 50 that in this particular embodiment is attached to a horseshoe-shaped registration device 51 designed to fit in a dental patient's mouth/jaw. The registration device has fiducial markers 6 on it so that a tracking system can sense the position of the registration device. As can be seen from FIG. 3, calibration device 50 may have a round recess or notch 55 for receiving a round end of an apparatus of the present invention. The calibration device 50, in this embodiment, may be situated between the horseshoe-shaped part that goes into a patient's mouth and the part that remains external to the patient's mouth. The external part 52 may have a series of markers 5, for example LEDs for tracking by a sensor of the tracking system of the image-guided system. The calibration device 50 may include at least the round notch/recess 55 plus at least a portion of a device containing this notch. In some preferred embodiments, the calibration device 50 may be defined to also include a registration device 51 and/or the external part 52.

As shown in FIG. 4, the present invention may be described as an apparatus 20 or tip extension 20 for use with an image-guided system that is designed to calibrate a handpiece having a tip. Tip extension 20 may have an attachment end 22 and a round end 24, the attachment end 22 configured to fixedly attach to the tip 44 of the handpiece (shown in FIG. 1). The attachment end 22 may include a female component 23 that may mate with a correspondingly shaped male component 43 of the tip 44 of the handpiece (shown in FIG. 1), or with a portion of the tip 44 or the entire tip 44. Female component 23 may be removably detachable from and re-attachable to the remainder 21 of the attachment end 22 by any suitable means 99 that affixes the female component 23 rigidly to the remainder component 21. FIG. 4 schematically illustrates the attachment end 22 as being substantially rectangular, but this is not a limitation since attachment end 22 may assume other shapes, such as for example cylindrical, flattened cylindrical, or other shapes. Preferably, attachment end 22 is shaped so as to have a distal surface 22A that is substantially straight and perpendicular to the sides (or at least to the distal ends of the sides) of attachment end 22. FIG. 4A shows a side view of tip 44 showing attachment means 99A used to connect the female component 23 to tip 44.

The round end 24 of tip extension 20 may be at least hemispherical, and may in fact be spherical in a preferred embodiment. In another preferred embodiment, round end 24 may be round in at least one dimension, and may be conical, for example with the wider base of the cone closer to neck 25. The round end 24 should be sufficiently spherical that round end 24 can be made to rotate when inserted into a calibration recess 55 such as notch 55 shown generally in FIG. 3. During such rotation, a center point of round end 24 may remain constant, i.e. fixed (not moving). One example of a typical diameter of round end 24, in one preferred embodiment, is two to four millimeters, or in a particular preferred version, three millimeters.

As shown in FIG. 4, tip extension 20 also is shown as having a neck 25, the neck 25 having a diameter that may be smaller than a diameter of the round end 24. In some preferred embodiments, the neck 25 may have a diameter that does not exceed half a diameter of the round end, or in other preferred embodiments does not exceed one-third, or 25% or 15% or 10% or 5% (or two-thirds) of the diameter of the round end 24. Neck 25 of tip extension 20 may be configured in overall shape and diameter to allow rotation of round end 24 when round end 24 is in a round recess such as calibration notch 55 (FIG. 3). "Round recess" means round in at least one dimension, and for example may be at least hemispherical and may be substantially spherical. A conical recess having a round end (the round end being the end closer to the tip extension 20 being inserted into that end) fits the definition of a "round recess". Such a conical recess would permit insertion and rotation of the handpiece 40 together with tip extension 20 and such rotation would not cause movement of the center point of round end 24. rather the center may remain constant, i.e. fixed (not moving). In particular, neck 25 may be configured to allow the rotation of the round end 24 when the round end is in a round recess such that a center 24C of the round end 24 remains stationary as the round end 24 rotates while contacting notch 55. This may allow the image-guided system to which the handpiece is connected or associated to calibrate the location of the center 24C of round end 24 and by extrapolation the end of the handpiece (including the tip extension). As can be seen from FIG. 4, neck 25 may be situated between the attachment end 22 and the round end 24. Attachment end 22 may be wider than the neck 25 since the attachment end 22 may need to surround tip 44 so as to allow the female component 23 to mate with tip 44 or a portion of tip 44 or with a male component 43 of tip 44. Male component 43 of tip 44 may simply be the portion of tip 44, for example the last two-thirds of the length of tip 44 or the last X millimeters or centimeters of the tip 44.

FIG. 5 shows an example of the tip extension 20 mating with the male component 43 of a tip 44 and showing a line of action. L running through a center of action C. As can be seen, attachment end 22 may be long enough (sometimes referred to as "thick" enough) along its longitudinal axis (parallel to the line L or axis of action L) (i.e. thick enough) to include or encompass the center of action C.

In some preferred embodiments, the present invention may be defined to include both tip extension 20 and also a calibration device such as shown in FIG. 3. Calibration device 50 is defined to be a component that is shaped to receive the round end 24 of attachment end 22 of tip extension 20. As such, calibration device 50 may comprise a round notch or recess 55. The round recess 55 may be round in at least one dimension and may be a conical, a spherical or substantially spherical recess, or at least hemispherical recess.

Figure 6A:
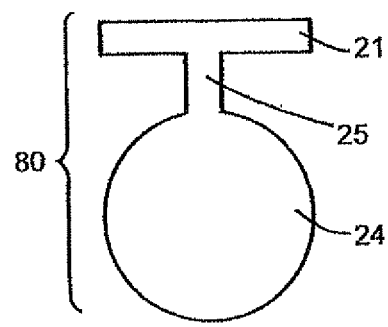
FIGS. 6A and 6B are schematic illustrations of a portion of an apparatus of the present invention, shown in two different configurations, in accordance with one embodiment of the present invention.
Figure 6B:
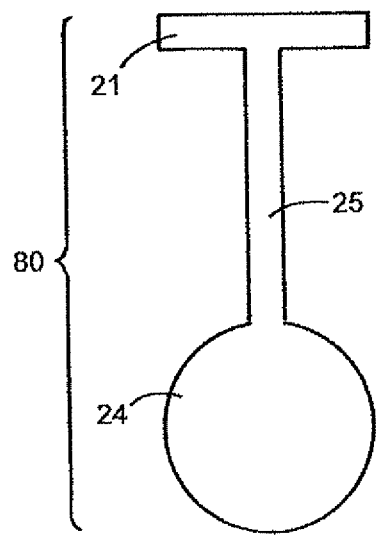

FIGS. 6A and 6B show one preferred embodiment of the ball tip 80 comprising the remainder 21 of attachment end 22 (FIG. 4), neck 25 and round end 24 of tip extension 20 including a longer version (FIG. 6B) and a shorter version (FIG. 6A). In one preferred embodiment of ball tip 80, the longer version of the combination, or of neck 25, may be fifteen millimeters longer than in the shorter version shown in FIG. 6A.

Figure 5A:
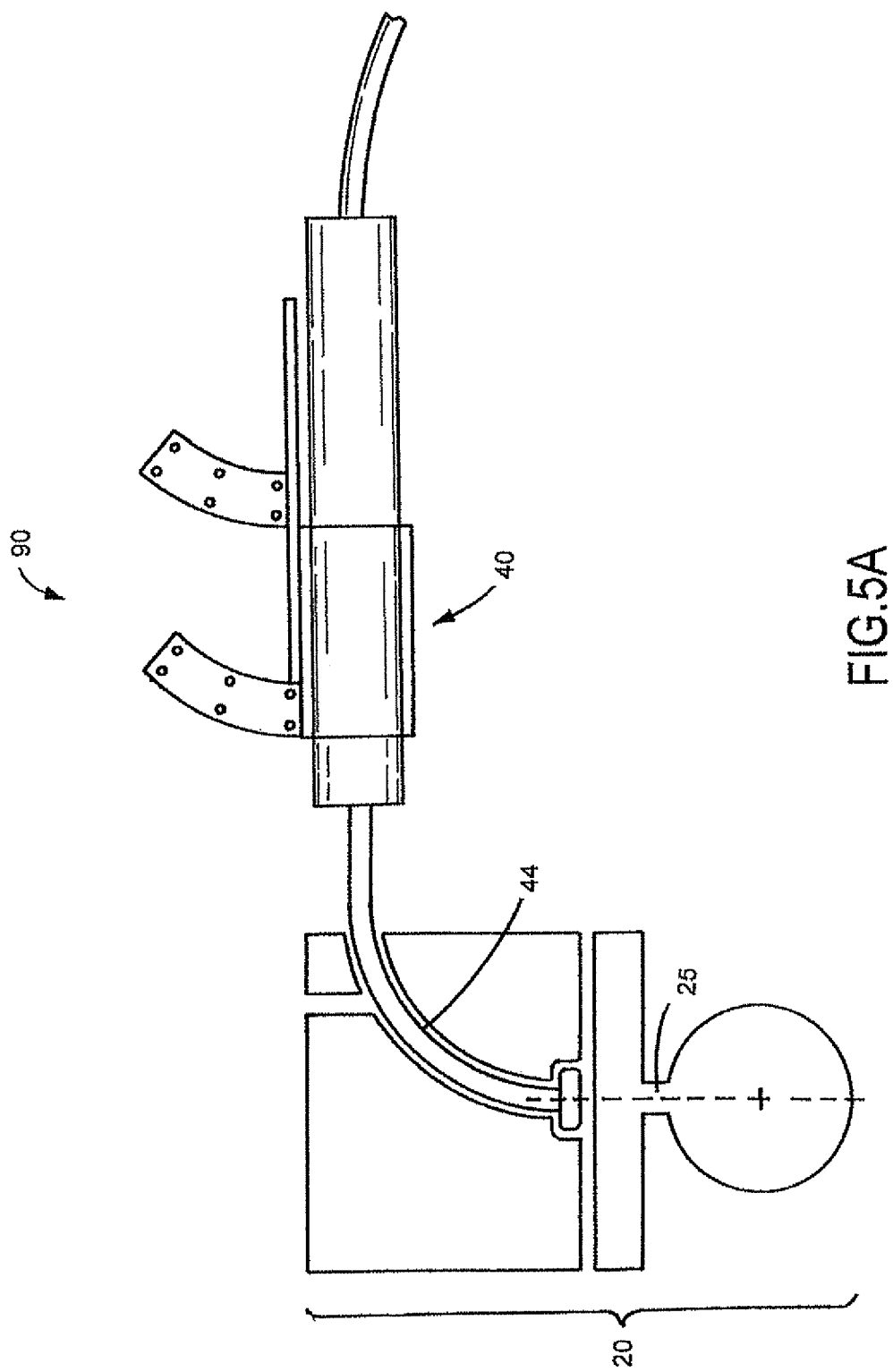
FIG. 5A is a schematic illustration of an apparatus of the present invention together with a handpiece, in accordance with one embodiment of the present invention.

The present invention may also be described as a tool for creating cavitation, for example in a bone. As shown in FIG. 5A, the tool 90 may comprise a handpiece such as handpiece 40 shown in FIG. 1 and having a tip such as tip 44 and may also comprise a tip extension 20 such as is shown in FIGS. 4-5. The tip 44 may be configured to emit one of (i) pressurized steam and (ii) ultrasonic energy waves, out of handpiece 40, in particular, out of tip 44. Tip 44 may be such that tip 44 does not lie on a line of action L of handpiece 40 (and may not lie on a longitudinal axis LH of the handpiece 40), for example, because tip 44 may be too curved or irregular.

Accordingly, tip 44 may be difficult to calibrate by a particular image-guided system or by known image-guided systems or position tracking systems. The tip extension 20 may have an attachment end 22 and a round end 24, the attachment end 22 fixedly attached to the tip 44. The round end 24 may be at least hemispherical, and preferably spherical. The tip extension 20 may have a neck 25 having a diameter smaller than a diameter of the round end 24, and may have the structural features described regarding tip extension apparatus 20.

The present invention may also be described as a tool 100 for cavitation, comprising a tip 44 of a handpiece, the tip 44 not lying on a longitudinal axis of action L of the handpiece 40 and configured to emit one of pressurized steam and ultrasonic energy out of the handpiece 40; and a tip extension 20 that may have an attachment end 22 and a round end 24, the attachment end 22 fixedly attached to the tip 44. The tip 44 may be curved and configured to emit high pressure steam out of the handpiece 40.

Figure 7:
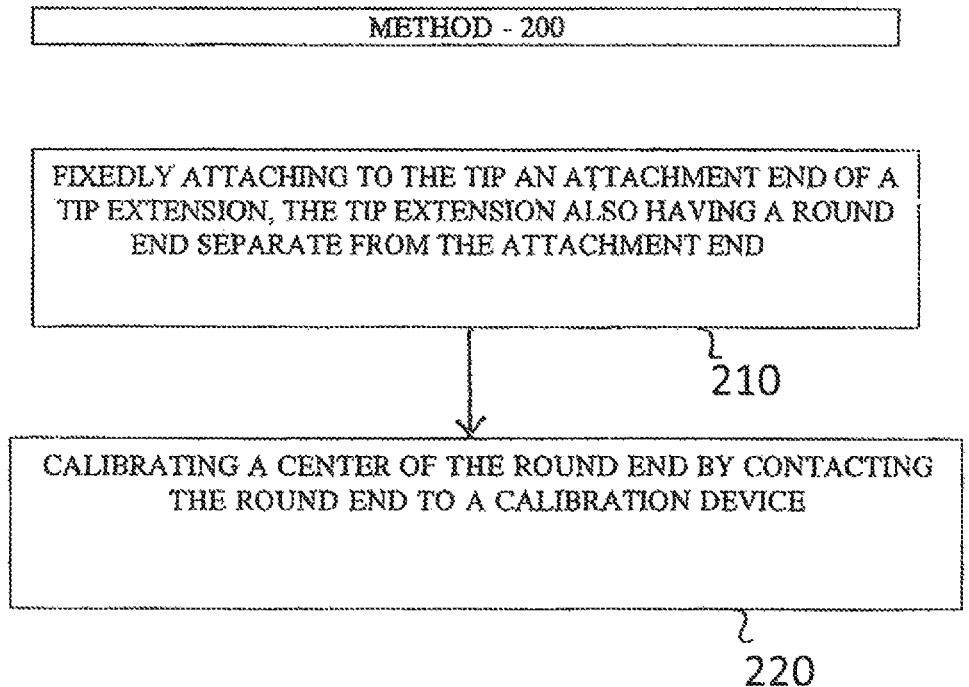
FIG. 7 is a flow chart showing a method in accordance with one embodiment of the present invention.

As seen from FIG. 7, the present invention can also be described as a method 200 of using an image-guided system to calibrate a handpiece having a tip. Method 200 may have a step 210 of fixedly attaching to the tip an attachment end 22 of a tip extension 20. The tip extension 20 may also have a round end 24 separate from the attachment end 22. Method 200 may also include a step 220 of calibrating a center of the round end 24 by contacting the round end to a calibration device, for example calibration device 55. Method 200 may also involve the fixedly attaching of the attachment end 22 to the tip 44 such that the attachment end comprises a female component 23 that mates with a correspondingly shaped male component 43 of the tip 44. Method 200 may have a step, in some versions, of having the calibrating of the center of the round end include touching the round end to a round notch while the tip extension is attached to the tip of the handpiece. This may further comprise rotating the round end while the round end is in contact with the round notch to calibrate a point at a center of the round end that remains stationary as the round end rotates. This may allow the image-guided system to track and store a position of the center of the round end. Doing so may thereby allow the image-guided system to calculate a position of the center of action, which in turn may allow the system to guide the surgeon to properly place the end of the tip of the handpiece relative to the working surface of the bone to be cut, for example a tooth. Accordingly, a further step of method 200 may be having the image-guided system calibrate a center of action of the handpiece from the calibration of the center of the round end.

In method 200, the tip may be curved or may be configured to assume any other irregular shape, for example such that the tip (or the line of action) is not aligned with an axis of action of handpiece 40. In some versions of the method 200 or method 300 or 400 or of the tip extension 20 (with or without calibration device 50) or tool 90 or tool 100, the final 0.1 millimeters (or in other preferred embodiments the final 0.3 or 0.5 or 0.05 mm or 0.01 mm) of the tip is not aligned with a longitudinal axis of the handpiece. Accordingly, the image-guided system may be unable to calibrate the tip without the method.

In some versions of method 200, the fixedly attaching of the attachment end of the tip extension to the tip may comprise mating the tip with a detachable female component of the attachment end and then attaching the female component to a remainder of the attachment end.

Figure 8:
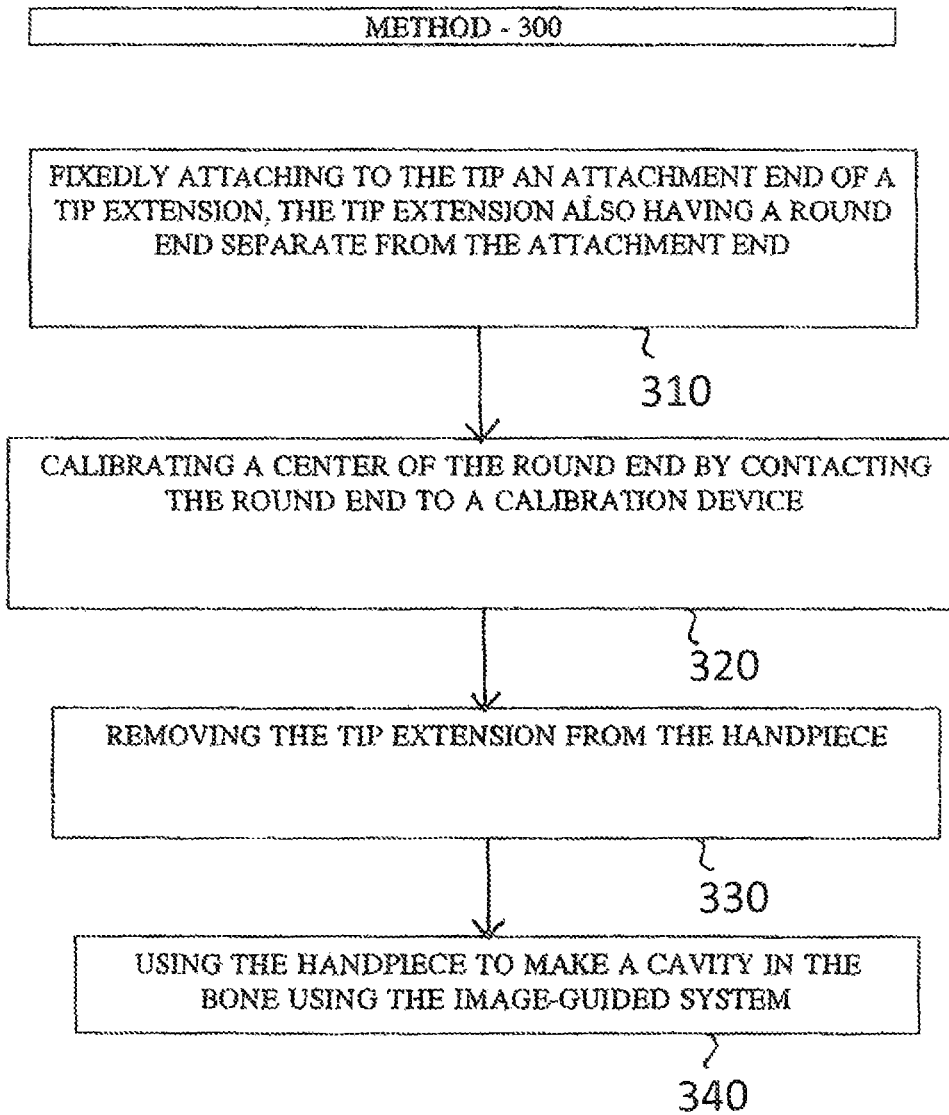
FIG. 8 is a flow chart showing a further method in accordance with one embodiment of the present invention.

As shown in FIG. 8, the present invention may also be described as a method 300 of cavitation of a bone of a human or animal using an image-guided system to calibrate a handpiece having a tip. Method 300 may include a step 310 of fixedly attaching to the tip an attachment end of a tip extension for example tip extension 20, the tip extension also having a round end separate from the attachment end. Another step 320 of method 300 may be calibrating a center of the round end by contacting the round end to a calibration device. Method 300 may also comprise a step 330 of removing the tip extension from the handpiece and a step 340 of using the handpiece to make a cavity in the bone using the image-guided system.

Some versions of method 300 may involve having the image-guided system calibrate a center of action of the handpiece from the calibration of the center of the round end and using the handpiece to make the cavity while maintaining the handpiece at a distance from a working surface of the bone consistent with a distance between the center of action and the tip. Other versions of method 300 may involve having the calibrating of the center of the round end include touching the round end to a round notch while the tip extension is attached to the tip of the handpiece and may involve rotating the round end while the round end is in contact with the round notch to calibrate a point at a center of the round end that remains stationary as the round end rotates.

As seen from FIG. 9, the present invention may also be described as a method 400 of making tip extensions suitable for a variety of handpieces made by a plurality of different manufacturers and that have a defined center of action that may vary from one manufacturer to another. Each of the handpieces may have a tip such that the tip does not lie on the line of action of the handpiece (and it may be such that the line of action is not parallel to the longitudinal axis of the handpiece), or in other versions such that the tip is too curved or irregular to be calibrated by a particular image-guided system. Method 400 may include a step 410 of providing a plurality of tip extensions, each tip extension of the plurality of tip extensions having an attachment end and a round end, the attachment end fixedly attachable to the tip of at least a plurality of the handpieces, the round end configured to be calibrated for the image-guided system by inserting the round end in a calibration device having a round recess. In a preferred embodiment, providing means selling or manufacturing (or arranging for the manufacture).

Method 400 may also comprise a step 420 of configuring particular tip extensions to be usable with particular handpieces of the variety of handpieces by configuring a length of each of a plurality of the particular tip extensions such that a distance from the center of action to a center of the round end remains constant. For example, a longer version having neck 25 shown in FIG. 6B may be for example fifteen millimeters longer than a shorter version having shorter neck 25 shown in FIG. 6A. In some versions of method 400, there may also be a step of maintaining constant a diameter of the round end of each tip extension of the plurality of tip extensions.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method of using an image-guided system to calibrate a handpiece having a tip at an active end of the handpiece, the tip not aligned with a line of action of the handpiece and the tip having a line of action in a direction of a resultant force of that which is emitted through the tip, the tip having a center of action spaced apart from the tip, the method comprising:

fixedly attaching to the tip an attachment end of a tip extension, the tip extension also having a round end separate from the attachment end, such that a center of the round end is substantially aligned with the center of action and such that a female component of the attachment end mates with a correspondingly shaped male component of the tip and such that after the fixedly attaching a vertical axis of the tip extension running from a distal surface of the tip to the center of the round end is aligned with the line of action of the tip; and calibrating the center of the round end by contacting the round end to a calibration device.

2. The method of claim 1, further comprising configuring the fixed attachment such that a combination of the female component and the male component, after fixed attachment, has a boxy shape.

3. The method of claim 2, wherein a width of the boxy-shaped combination exceeds a diameter of the round end.

4. The method of claim 1, wherein the calibrating of the center of the round end includes touching the round end to a round notch while the tip extension is attached to the tip of the handpiece.

5. The method of claim 4, further comprising rotating the round end while the round end is in contact with the round notch to calibrate a point at a center of the round end that remains stationary as the round end rotates.

6. The method of claim 1, further comprising having the image-guided system calibrate the center of action of the handpiece from the calibration of the center of the round end.

7. The method of claim 1, wherein the image-guided system is unable to calibrate the tip without the method.

8. The method of claim 1, wherein fixedly attaching the attachment end of the tip extension to the tip comprises mating the tip with a detachable female component of the attachment end and then attaching the female component to a remainder of the attachment end.

9. The method of claim 1, wherein a final 0.1 millimeters of the tip is not aligned with a longitudinal axis of the handpiece.

10. A method of cavitation of a bone of a human or animal using an image-guided system to calibrate a handpiece having a tip at an active end of the handpiece, the tip not aligned with a line of action of the handpiece, the tip having a center of action spaced apart from the tip, the method comprising:

fixedly attaching to the tip an attachment end of a tip extension, the tip extension also having a round end separate from the attachment end, a center of the round end substantially aligned with the center of action, such that a female component of the attachment end mates with a correspondingly shaped male component of the tip and such that after the fixedly attaching a vertical axis of the tip extension running from a distal surface of the tip to the center of the round end is aligned with the line of action of the tip;

calibrating the center of the round end by contacting the round end to a calibration device;

removing the tip extension from the handpiece; and using the handpiece to make a cavity in the bone using the image-guided system.

11. The method of claim 10, further comprising having the image-guided system calibrate the center of action of the handpiece from the calibration of the center of the round end and using the handpiece to make the cavity while maintaining the handpiece at a distance from a working surface of the bone consistent with a distance between the center of action and the tip.

12. The method of claim 11, wherein the calibrating of the center of the round end includes touching the round end to a round notch while the tip extension is attached to the tip of the handpiece.

13. The method of claim 12, further comprising rotating the round end while the round end is in contact with the round notch to calibrate a point at a center of the round end that remains stationary as the round end rotates.

14. A method of making tip extensions suitable for a variety of handpieces made by a plurality of different manufacturers and that have a defined center of action that may vary from one manufacturer to another, each of the handpieces having a tip at an active end of the handpiece such that the tip is not aligned with a line of action of the handpiece and such that a center of action of the tip is spaced apart from the tip, the method comprising:

providing a plurality of tip extensions, each tip extension of the plurality of tip extensions having an attachment end and a round end, a center of the round end substantially aligned with the center of action, the attachment end fixedly attachable to the tip of at least a plurality of the handpieces such that a female component of the attachment end mates with a correspondingly shaped male component of the tip in a manner that a vertical axis of the tip extension running from a distal surface of the tip to the center of the round end is aligned with the line of action of the tip, the round end configured to be calibrated for an image-guided system by inserting the round end in a calibration device having a round recess; and configuring particular tip extensions to be usable with particular handpieces of the variety of handpieces by configuring a length of each of a plurality of the particular tip extensions such that a distance from the center of action to a center of the round end remains constant.

15. The method of claim 14, further comprising maintaining constant a diameter of the round end of each tip extension of the plurality of tip extensions.

16. An apparatus configured for use with an image-guided system to calibrate a handpiece having a tip at an active end of the handpiece, the tip not aligned with a line of action of the handpiece, a line of action of the tip in a direction of a resultant force of that which is emitted through the tip, the tip having a center of action spaced apart from the tip, the apparatus comprising:

a tip extension having an attachment end and a round end, a center of the round end substantially aligned with the center of action, the attachment end configured to fixedly attach to the tip of the handpiece such that a female component of the attachment end mates with a correspondingly shaped male component of the tip and such that after the fixed attachment a vertical axis of the tip extension running from a distal surface of the tip to the of the round end is aligned with the line of action of the tip.

17. The apparatus of claim 16, wherein a combination of the female component and the male component, after fixed attachment, has a boxy shape.

18. The apparatus of claim 17, wherein the female component is detachable from a remainder of the attachment end.

19. The apparatus of claim 16, wherein the round end is at least hemispherical.

20. The apparatus of claim 16, wherein the round end is spherical.

21. The apparatus of claim 16, wherein the tip extension has a neck, the neck having a diameter smaller than a diameter of the round end.

22. The apparatus of claim 16, wherein the tip extension has a neck, the neck having a diameter that does not exceed half a diameter of the round end.

23. The apparatus of claim 16, wherein the tip extension has a neck configured to allow rotation of the round end when the round end is in a round recess.

24. The apparatus of claim 23, wherein the neck is configured to allow the rotation of the round end when the round end is in a round recess such that a center of the round end remains stationary as the round end rotates.

25. The apparatus of claim 23, wherein the neck is situated between the attachment end and the round end and wherein the attachment end is wider than the neck.

26. The apparatus of claim 23, wherein the neck is situated between the attachment end and the round end and wherein the attachment end is thick enough to include a center of action.

27. The apparatus of claim 16, further comprising a calibration device, the calibration device having a round recess.

28. The apparatus of claim 27, wherein the round recess is a substantially spherical recess.

29. The apparatus of claim 27, wherein the round recess is at least hemispherical.

30. The apparatus of claim 27, wherein the round recess is conical.

31. The apparatus of claim 16, wherein the center of action is spaced apart from the tip by a distance of half a millimeter or more.

32. A tool for cavitation, comprising:
a handpiece having a tip configured to emit one of pressurized steam and ultrasonic energy waves out of the handpiece, the tip not lying on a line of action of the handpiece, the tip not aligned with a line of action of the handpiece, the line of action of the tip defined to be a direction of a resultant force of that which is emitted through the tip, the tip having a center of action spaced apart from the tip; and
a tip extension having an attachment end and a round end, a center of the round end substantially aligned with the center of action, the attachment end configured to fixedly attach to the tip of the handpiece such that a female component of the attachment end mates with a correspondingly shaped male component of the tip and such that after the fixed attachment a vertical axis of the tip extension running from a distal surface of the tip to the center of the round end is aligned with the line of action of the tip.

33. A tool for cavitation, comprising:
a handpiece having a tip at an active end of the handpiece, the tip not aligned with a line of action of the handpiece, the tip having a line of action in a direction of a resultant force of that which is emitted through the tip and having a center of action spaced apart from the tip; and
a tip extension having an attachment end and a round end, a center of the round end substantially aligned with the center of action, the attachment end fixedly attached to the tip of the handpiece such that a female component of the attachment end mates with a correspondingly shaped male component of the tip and such that after the fixed attachment a vertical axis of the tip extension running from a distal surface of the tip to the center of the round end is aligned with the line of action of the tip.

34. The tool of claim 33, wherein the round end is at least hemispherical.

35. The tool of claim 33, wherein the tip extension has a neck, the neck having a diameter smaller than a diameter of the round end and smaller than a width of the attachment end.

36. The tool of claim 33, wherein the tip extension has a neck, the neck having a diameter that does not exceed half a diameter of the round end and the neck being smaller than a width of the attachment end.

37. The tool of claim 33, wherein the tip extension has a neck configured to allow rotation of the round end when the round end is in a round recess.

38. The tool of claim 37, wherein the neck is configured to allow the rotation of the round end when the round end is in a round recess such that a center of the round end remains stationary as the round end rotates.

39. A tool for cavitation, comprising:
a tip of a handpiece, the tip not lying on a line of action of the handpiece and configured to emit one of pressurized steam and ultrasonic energy out of the handpiece, the tip having a line of action in a direction of a resultant force of that which is emitted through the tip and having a center of action spaced apart from the tip; and
a tip extension having an attachment end and a round end, a center of the round end substantially aligned with the center of action, the attachment end fixedly attached to the tip of the handpiece such that a female component of the attachment end mates with a correspondingly shaped male component of the tip and such that after the fixed attachment a vertical axis of the tip extension running from a distal surface of the tip to the center of the round end is aligned with the line of action of the tip.

40. The tool of claim 39, wherein the tip is curved and configured to emit high pressure steam out of the handpiece.

41. The tool of claim 39, wherein a combination of the female component and the male component, after fixed attachment, has a boxy shape.

* * * * *